United States Patent [19]

Ito et al.

[11] 4,418,524

[45] Dec. 6, 1983

[54] TWISTED YARN AND TWISTED BUNDLE OF YARNS

[75] Inventors: Osamu Ito, Utsunomiya; Kazunori Nishizawa, Funabashi, both of Japan

[73] Assignee: Kao Soap Co., Ltd., Tokyo, Japan

[21] Appl. No.: 274,124

[22] Filed: Jun. 16, 1981

[30] Foreign Application Priority Data

Jun. 19, 1980 [JP] Japan .................................. 55-83390
Apr. 27, 1981 [JP] Japan .................................. 56-63602

[51] Int. Cl.$^3$ .......................... D02G 3/38; D02G 3/04
[52] U.S. Cl. ...................................... 57/239; 57/238; 57/244; 57/245
[58] Field of Search ................. 57/210, 211, 236, 238, 57/239, 243, 244, 245; 28/178, 247

[56] References Cited

U.S. PATENT DOCUMENTS

| | | | |
|---|---|---|---|
| 2,656,585 | 10/1953 | Jackson | 57/239 X |
| 2,979,883 | 4/1961 | Waltz | 57/244 X |
| 3,396,528 | 8/1968 | Weiss | 57/239 |
| 3,604,470 | 9/1971 | Zindwer | 57/239 X |

OTHER PUBLICATIONS

America's Textiles, vol. 6, Feb. 1977.

*Primary Examiner*—Donald Watkins
*Attorney, Agent, or Firm*—Flynn, Thiel, Boutell & Tanis

[57] ABSTRACT

A twisted combination yarn is disclosed which is made of a first yarn which contracts when it absorbs water, and a second yarn plied with the first yarn which is not substantially changed in length by contact with water. The twisted combination yarn of the invention has a high water absorbing capacity, and contracts and becomes elastic when it absorbs water.

23 Claims, 9 Drawing Figures

TWISTED YARN AND TWISTED BUNDLE OF YARNS

The present invention relates to a twisted yarn and a twisted bundle of yarns by which said yarn of the twisted bundle or at least one yarn is contracted in contact with water and at the same time provided with elasticity.

A twisted combination yarn is a twisted yarn having new properties, which is formed by twisting together at least two kinds of twisted yarns, single yarns, mixtwisted yarns or spun yarns, and at the present, there are marketed various twisted combination yarns formed by twisting various twisted yarns or single yarns. For example, there is known a twisted combination yarn formed by twisting a cotton yarn and a chemical fiber yarn together so as to impart the good properties of both the yarns, such as good washability and good feel, to the resulting twisted combination yarn.

We made researches on these twisted combination yarns and we found that a yarn formed of water-swelling fibers is shrunk and rendered elastic when it absorbs water and when this yarn is mix-twisted with other non-shrinkable yarn, there can be obtained a twisted combination yarn having new functions, which can advantageously be used in various fields. We have now completed the present invention based on this finding.

It is a primary object of the present invention to provide a twisted combination yarn which is shrunk when it absorbs water.

Another object of the present invention is to provide a water-absorbing, twisted combination yarn which has an excellent strength even when it absorbs water.

Still another object of the present invention is to provide a twisted combination yarn which is rendered elastic when it absorbs water.

In accordance with the present invention, these objects can be attained by a twisted combination yarn comprising at least two kinds of twisted yarns, single yarns or mix-twisted yarns, which are twisted together, wherein at least one yarn is a spun yarn (water-absorbing shrinkable yarn) consisting of a twisted yarn, a single yarn or a mix-twisted yarn which has a water-absorbing property and is shrunk in the direction of the yarn length, preferably by at least 10% of the original length, when it absorbs water, and at least one other yarn is a spun yarn (non-shrinkable yarn) consisting of a twisted yarn, a single yarn or a mix-twisted yarn which is not substantially shrunk on contact with water.

This twisted combination yarn of the present invention is shrunk and rendered elastic when it absorbs water, and since the yarn of the present invention is reinforced by the non-shrinkable yarn, the yarn of the present invention is excellent in strength. Accordingly, the foregoing objects can be attained by the present invention.

In the twisted combination yarn of the present invention, as the water-absorbing shrinkable yarn, there can be used, for example, yarns of modification products of cellulose fibers of cotton, rayon and the like, such a carboxymethylated cotton, methylated cotton, ethylated cotton, hydroxyethylated cotton, sulfated cotton, sulfonated cotton, phosphated cotton, cationized cotton, amphoterically ionized cotton, cellulose fibers grafted with sodium acrylate, acrylic acid, acrylonitrile and acrylamide and crosslinking products thereof, and similar modification products of wool, silk and the like and modified synthetic fibers, such as partially saponified acrylonitrile type fibers and fibers of Vinylon partially esterified with maleic acid.

As the non-shrinkable yarn (shrunk by less than 10% on contact with water), there can be used, for example, yarns of synthetic fibers such as nylon fibers, acrylic fibers, Vinylon fibers, polyester fibers and polypropylene fibers, semi-synthetic fibers such as rayon fibers and acetate fibers and natural fibers such as hemp fibers, cotton fibers, wool fibers and silk fibers.

BRIEF DESCRIPTION OF THE DRAWINGS

In the twisted combination yarn of the present invention, properties manifested in case of soft twisting (for example, 5 twists per inch) are different to some extent from properties manifested in case of strong twisting (for example, 10 twists per inch). This aspect will now be described with reference to the accompanying drawings. FIG. 1 is a diagram illustrating the state of a loosely twisted combination yarn, in which reference numeral 1 represents a non-shrinkable yarn and reference numeral 2 represents a water-absorbing shrinkable yarn. FIG. 2 is a diagram illustrating the state of the twisted combination yarn of FIG. 1 which has absorbed water. Large voids are formed around the water-absorbing shrinkable yarn 2' which has absorbed water. Accordingly, in the loosely twisted combination yarn, the water-retaining property is increased and the elastic property is manifested when it absorbs water. FIG. 3 is a diagram illustrating the state of a strongly twisted combination yarn, and FIG. 4 is a diagram illustrating the state of the twisted combination yarn of FIG. 3 which has water. As shown in FIG. 4, the strongly twisted combination yarn of the present invention takes a sheath-like shape when it absorbs water, but it can be restored to the original length by the force acting in the direction of the yarn length. Accordingly, the yarn has a higher elastic property.

Figure 1:
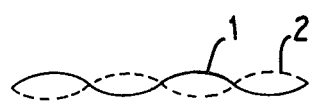
FIG. 1 is a side view diagrammatically illustrating a loosely twisted combination yarn according to the present invention.
Figure 2:
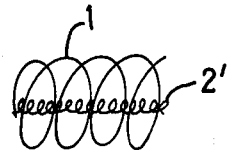
FIG. 2 is a side view diagrammatically illustrating the state where the twisted combination yarn shown in FIG. 1 absorbs water.
Figure 3:
FIG. 3 is a side view diagrammatically illustrating a strongly twisted combination yarn according to the present invention.
Figure 4:
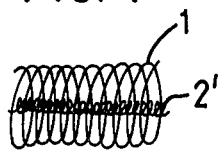
FIG. 4 is a side view diagrammatically illustrating the state where the twisted combination yarn shown in FIG. 3 absorbs water.

The twisted combination yarn of the present invention can be used in various fields by adjusting the degree of twisting appropriately. Typical instances of applications of the twisted combination yarn of the present invention will now be described.

As one application of the present invention, there can be mentioned a water-absorbing article. In the case where the twisted combination yarn of the present invention is used for a water-absorbing article such as a sanitary napkin, a tampon, a disposable diaper or the like, when the absorbing article is wetted with excreta, voids are formed around the twisted combination yarn, and this absorbing article is advantageous in that large quantities of excreta can be retained in these voids. For example, if the twisted yarn of the present invention is stitched in the surface layer, i.e. non-woven fabric, of a sanitary napkin or disposable diaper, the twisted yarn which contracts upon absorption of water is wetted and thereby contracted with the drainage from the human body is passed through the surface layer and absorbed by an absorbent. As a result, the surface layer becomes uneven to form cavities between the body of the user and the absorbent to make the user comfortable.

As another application of the present invention, there can be mentioned a disposable diaper having an elastic member formed on the edge of the peripheral part of the crotch portion. Namely, the twisted combination yarn of the present invention can be used instead of this elastic member. Since conventional elastic members used in this field always have an elastic property, they involve various problems in connection with usage, preparation process and transportation thereof. More specifically, while a diaper is actually used, the crotch portion is always sealed by such elastic member and becomes musty. Moreover, since the crotch portion is always compressed by the elastic member, the wearing feel is not good. In the manufacture of these diapers, such elastic member is attached to the diaper in the state where the elastic member is stretched, and this operation involves various difficulties and the manufacturing efficiency is therefore reduced. In the product diaper, the elastic member is kept shrunk, and therefore, the entire diaper is wrinkled and the product per se is bulky, with the result that the transportation cost is increased. In contrast, when the twisted combination yarn of the present invention is used instead of such elastic member, the foregoing defects can effectively be eliminated. For example, since the yarn of the present invention is not elastic in the ordinary state, a certain space is formed around the crotch portion while the diaper is used, and the crotch portion is prevented from getting musty. However, since the yarn of the present invention is shrunk and is rendered elastic when wetted with urine, the edge of the diaper is caused to adhere to the crotch portion because of the shrunk yarn of the present invention and leakage of urine can effectively be prevented. Furthermore, in the manufacture of diapers, since the twisted combination yarn of the present invention is attached to the diaper while it is not elastic at all (while it is dry), reduction of the manufacturing efficiency is not brought about. Moreover, the product diaper is not wrinkled at all because the twisted combination yarn is not elastic before it is used, and the product diaper is not bulky at all. Therefore, the transportation cost can be reduced.

As still another application of the present invention, there can be mentioned a knitted or woven fabric. For example, the twisted combination yarn of the present invention can be used for manufacture of a knitted or woven fabric for swimming suits. Presently marketed swimming suits are strongly elastic so that they fit the body, but some swimming suits, for example, knit suits, become loose when they are wetted with water. In contrast, swimming suits of a woven or knitted fabric formed completely or partially of the twisted combination yarn of the present invention are loose before they are wetted with water, but when they are wetted with water, the twisted combination yarn is shrunk and the swimming suit fits the body. Since the original state is restored in the twisted combination yarn after drying, it can be used many times repeatedly.

The twisted combination yarn of the present invention can be used for various valuable applications other than those described above.

As above discussed, carboxymethylated cellulose is most preferable as a water-absorbing, shrinkable yarn. According to further study of the inventors, it has been made apparent that the stretchability of carboxymethylated cellulose upon absorption of water depends on carboxymethylation degree of twisting strength, i.e. twist coefficient, of the carboxymethylated cellulose yarn.

More particularly, the higher the carboxymethylation degree (hereinafter referred to as D.S.) and the higher the twist coefficient, the higher the stretchability of the twisted yarn.

For attaining the above-mentioned purposes of the present invention, D.S. of the carboxymethylated cellulose single yarn is preferred to be from 0.15 up to 0.4. A single yarn is previously twisted generally to have so called pre-twist. When the pre-twist is insufficient, however, a further twisting is preferred to attain a twist coefficient of at least 3.0. The twist is determined according to the following formula:

$$K = \frac{T}{\sqrt{N}}$$

wherein

K represents a twist coefficient,

T represents number of twists per inch, and

N represents a count No. of the yarn (if number of yarns of count No. n to be twisted is l, N equals n/l)

(If plural yarns are intertwisted, the pre-twist turns are not included in the number of twists. If a single yarn is used, the pre-twist turns are included in the number of twists).

Further, the above-mentioned improvement of the present invention can be attained by crosslinking the single yarn of carboxymethylated cellulose, without dissolution, even if the carboxymethylated cellulose single yarn has a high carboxymethylation degree. In case such a crosslinked carboxymethylated cellulose yarn is used, the improvements of the present invention are attained by controlling the D.S. to 0.25–0.70 and twist coefficient to at least 3.0.

The twisted yarn of the present invention can be obtained also by twisting plural carboxymethylated cellulose single yarns having the above carboxymethylation degree to attain a twist coefficient of at least 3.0 or by twisting the carboxymethylated cellulose single yarn with another water-unabsorbing, contracting yarn such as cotton, rayon or synthetic fiber yarn to attain a twist coefficient of at least 3.0. In such a case, however, the carboxymethyllated cellulose yarn should be used in an amount of at least 50 wt. %. If the water-unabsorbing, contracting yarn is used in an amount of more than 50%, the contracting power of the product is reduced unfavorably. In case plural single yarns are to be intertwisted, it is preferred that the direction of twist is the same as the direction of the pre-twist. However, the directions may also be contrary to each other.

As examples of the carboxymethylated cellulose yarns used in the present invention, there may be mentioned carboxymethylated yarns of cotton and polynosic rayon celluloses.

As crosslinking agents used for obtaining the crosslinked, carboxymethylated cellulose yarns, there may be mentioned glyoxal, epichlorohydrin, ethylene glycol and glycidyl ether.

The single yarn of carboxymethylated cellulose as mentioned above exhibits an excellent stretchability, namely a contraction power of at least 10 g and a contraction coefficient of at least 10% upon absorption of water. The yarn which contracts upon absorption of water is provided with a high strength.

The present invention will now be described in detail with reference to the following Examples that by no means limit the scope of the present invention. Examples of production of water-absorbing shrinkable yarns that can be used in the present invention are first described.

PRODUCTION EXAMPLE 1 (CARBOXYMETHYLATED COTTON)

In a reactant solution comprising 0.8 g of NaOH, 1.83 g of $ClCH_2COONa$ and 60 g of 80% ethanol was immersed 0.3 g of a cotton yarn (Daruma Tacking Thread 40/3), and the yarn was allowed to stand in the solution at room temperature for 1 hour. Then, reaction was conducted at 60° C. for 6 hours and the treated yarn was neutralized with acetic acid. Then, the yarn was washed 3 times with 80% ethanol and 1 time with ethanol, and the yarn was dried. The etherification degree was 0.35 in the resulting carboxymethylated cotton yarn.

PRODUCTION EXAMPLE 2 (METHYLATED COTTON)

In 100 ml of a 30% aqueous solution of NaOH was immersed 2.0 g of a cotton yarn (Daruma Tacking Thread) in a nitrogen atmosphere at room temperature for 1 hour. The yarn was compressed so that the compression ratio was 3, and excessive NaOH was removed. Then, the yarn was charged in 100 ml of toluene and 5 ml of dimethyl sulfate was dropped therein over a periof of 1 hour with stirring. The mixture was stirred for 10 hours at room temperature and toluene was removed from the yarn. Then, the yarn was neutralized with acetic acid. The yarn was dried with 80% methanol (water/methanol ratio=20/80) and dried. The etherification degree was 0.3 in the resulting methylated cotton yarn.

PRODUCTION EXAMPLE 3 (SULFATED COTTON)

In a reactant solution (comprising 0.63 g of ammonium sulfate, 13 ml of 1-butanol and 35 ml of 95% sulfuric acid) cooled to 0° C. was immersed 2.5 g of cotton yarn (Daruma Tacking Thread) at 0° C. for 20 minutes. Then, the thread yarn was taken out and dispersed in 50% methanol (water/methanol ratio=50/50) and neutralized at 0° C. with a 5% aqueous solution of acetic acid, and then, the yarn was washed with 80% methanol (water/methanol ratio=20/80) and dried on calcium chloride under reduced pressure.

The etherification degree was 0.2 in the resulting sulfated cotton yarn.

PRODUCTION EXAMPLE 4 (CATIONIZED COTTON)

In 38 g of 75% aqueous isopropyl alcohol containing 3.36 g of glycidyltrimethyl ammonium chloride was immersed 6.0 g of a cotton yarn (Daruma Tacking Yarn), and the temperature was elevated to 50° C. and 0.8 g of a 20% aqueous temperature was elevated to 50° C. and 0.8 g of a 20% aqueous solution of NaOH was added. Reaction was conducted at 50° C. for 9 hours and the yarn was neutralized with dilute hydrochloric acid. Then, the yarn was washed with 80% ethanol (water/MeOH ratio=20/80) and dried.

The cationization degree was 0.25 in the cationized cotton yarn.

PRODUCTION EXAMPLE 5 (PARTIALLY SAPONIFIED ACRYLIC FIBER)

In 95 g of a 15% aqueous solution of NaOH was immersed 5 g of an acrylonitrile type fiber, and the fiber was boiled with stirring for 30 minutes. The treated fiber was dispersed in a 50% aqueous solution, neutralized with acetic acid, washed with 80% methanol and dried. The obtained fiber was spun to a spun yarn having a count number of 30 as a water-absorbing shrinkable yarn.

The resulting partially saponified acrylic fiber contained 2.1 millimoles/g of —COONa groups.

Physical properties of the water-absorbing shrinkable yarns obtained in the above Production Examples in the state where they absorbed water are shown in Table 1.

The water-absorbing shrinkable yarns obtained in Production Examples 1 through 5 were mix-twisted with a cotton yarn (Daruma Tacking Thread) as the non-shrinkable yarn) at a twist number of 5 per inch to obtain twisted combination yarns (Examples 1 through 5) of the present invention. Properties of these yarns in the state where they absorbed water are shown in Table 2.

Incidentally, there are two methods for production of water-absorbing shrinkable yarns. According to one method, the yarn per se is reacted as in Production Examples 1, 2, 3 and 4, and according to the other method, the fiber is first reacted and then spun into a yarn. Either of these two methods can be adopted in the present invention.

TABLE 1

| | Water-Absorbing Shrinkable Yarns | | |
|---|---|---|---|
| Production Example No. | Percent Shrinkage* (%) | Initial Young's Modulus (dyne/cm$^2$) | Young's Modulus (dyne/cm$^2$) at Original Length | Tensile Strength (g) |
| 1 | 29 | $1.5 \times 10^6$ | $2.8 \times 10^7$ | 56.2 |
| 2 | 14 | $5.2 \times 10^6$ | $6.7 \times 10^7$ | 210 |
| 3 | 24 | $1.7 \times 10^6$ | $3.5 \times 10^7$ | 69.3 |
| 4 | 12 | $6.7 \times 10^6$ | $8.1 \times 10^7$ | 280 |
| 5 | 26 | $1.7 \times 10^6$ | $1.9 \times 10^7$ | 60.5 |

TABLE 2

| | Twisted Combination Yarns | | |
|---|---|---|---|
| Example No. | Percent Shrinkage* (%) | Initial Young's Modulus (dyne/cm$^2$) | Young's Modulus (dyne/cm) at Original Length | Tensile Strength (g) |
| 1 | 30 | $1.9 \times 10^6$ | $4.5 \times 10^7$ | 820 |
| 2 | 13 | $5.6 \times 10^6$ | $9.1 \times 10^7$ | 910 |

TABLE 2-continued

| | Twisted Combination Yarns | | | |
|---|---|---|---|---|
| Example No. | Percent Shrinkage* (%) | Initial Young's Modulus (dyne/cm²) | Young's Modulus (dyne/cm) at Original Length | Tensile Strength (g) |
| 3 | 22 | $2.3 \times 10^6$ | $4.9 \times 10^7$ | 880 |
| 4 | 11 | $7.1 \times 10^6$ | $9.8 \times 10^7$ | 950 |
| 5 | 26 | $1.8 \times 10^6$ | $3.7 \times 10^7$ | 740 |

Note
*percent shrinkage $= \dfrac{\text{original yarn length} - \text{yarn length on shrinkage}}{\text{original yarn length}} \times 100$ From the data shown in Tables 1 and 2, it is apparent that the obtained twisted combination yarns fully attain the objects of the present invention.

The present invention will now be described more in detail in the following Examples using a carboxymethylated yarn as the water-absorbing shrinkable yarn.

There are two methods for production of twisted combination yarns of the present invention. According to one method, a water-absorbing shrinkable yarn is first prepared and it is then mix-twisted with a non-shrinkable yarn, as shown in Examples 1 through 5 (two-stage method). According to the other method, a yarn which is to be reacted to form a water-absorbing shrinkable yarn, is twisted with a yarn which is not reacted with a reactant solution, and the twisted yarn is treated with the reactant solution to react the former yarn alone with the reactant solution (one-stage method).

EXAMPLE 6 (TWO-STAGE METHOD)

Water-absorbing shrinkable yarn:
  Carboxymethylated cotton yarn (Daruma Tacking Thread 40/3, twisted 3 yarns of count number of 40)
Non-shrinkable yarn:
  Cotton yarn (Daruma Tacking Thread)
  Water-absorbing shrinkable yarns were prepared in the same manner as described in Production Example 1 except that the reaction time was changed to 2, 4, 6 or 9 hours, and they were then mix-twisted with the non-shrinkable yarn.

The etherification degrees of the water-absorbing shrinkable yarns obtained by conducting the reaction for 2, 4, 6 and 9 hours were 0.12, 0.27, 0.35 and 0.40, respectively.

EXAMPLE 7 (ONE-STAGE METHOD)

Water-absorbing shrinkable yarn:
  Carboxymethylated carbon yarn (Daruma Tacking Thread 40/3, twisted 3 yarns of count number of 40)
Non-shrinkable yarn:
  Tacking thread of Vinylon
  The starting cotton yarn (Daruma Tacking Thread 40/3) was twisted with the non-shrinkable yarn, and the obtained mix-twisted yarn was carboxymethylated under the conditions used in Example 6.

EXAMPLE 8

Water-absorbing shrinkable yarn:
  Carboxymethylated and crosslinked cotton yarn (Daruma Tacking Thread 40/3)
Non-shrinkable yarn:
  Cotton yarn (Daruma Tacking Thread 40/3)
  The starting cotton yarn was carboxymethylated under the conditions shown in Production Example 1 and then crosslinked with glyoxal to obtain a water-absorbing shrinkable yarn.

The crosslinking reaction was carried out by immersing the carboxymethylated yarn in 80% ethanol in an amount 10 times (on the weight basis) the amount of the yarn, which contained 0.5, 1.0, 1.5 or 2.0%, based on 80% ethanol, of 40% glyoxal for 5 minutes with stirring, recovering the yarn by filtration and conducting reaction at 105° C. for 30 minutes.

The carboxymethylated and crosslinked, water-absorbing shrinkable yarn obtained by the above reaction was mix-twisted with the non-shrinkable yarn to obtain a twisted combination yarn.

Properties of the water-absorbing shrinkable yarns and twisted combination yarns obtained in Examples 6 through 8 are shown in Tables 3 and 4.

TABLE 3

| | | | | Water-Absorbing Shrinkable Yarns | | | | |
|---|---|---|---|---|---|---|---|---|
| Sample No. | Example No. | Reaction Time (hours) | D.S. | Amount (%) Cross-linked 40% Glyoxal | Percent Shrinkage (%) | Initial Young's Modulus (dyne/cm²) | Young's Modulus (dyne/cm²) at Original Length | Tensile Strength (%) |
| 1 | 6 | 2 | 0.12 | — | 17 | $4.3 \times 10^6$ | $5.9 \times 10^7$ | 170 |
| 2 | 6 | 4 | 0.27 | — | 24 | $1.6 \times 10^6$ | $3.5 \times 10^7$ | 51 |
| 3 | 6 | 6 | 0.35 | — | 29 | $1.5 \times 10^6$ | $2.8 \times 10^7$ | 56 |
| 4 | 6 | 9 | 0.40 | — | 35 | $1.6 \times 10^6$ | $2.3 \times 10^7$ | 63 |
| 5 | 8 | 6 | 0.35 | 0.5 | 33 | $1.6 \times 10^6$ | $3.3 \times 10^7$ | 67 |
| 6 | 8 | 6 | 0.35 | 1.0 | 32 | $2.0 \times 10^6$ | $3.0 \times 10^7$ | 64 |
| 7 | 8 | 6 | 0.35 | 1.5 | 30 | $2.3 \times 10^6$ | $3.4 \times 10^7$ | 73 |

TABLE 4

| | | | Twisted Combination Yarns | | | | |
|---|---|---|---|---|---|---|---|
| Sample No. | Example No. | Reaction Time (hours) | Twist Number per Inch | Percent Shrinkage (%) | Initial Young's Modulus (dyne/cm²) | Young's Modulus (dyne/cm²) at Original Length | Tensile Strength (%) |
| 1 | 6 | 6 | 5 | 30 | $1.9 \times 10^6$ | $4.5 \times 10^7$ | 820 |
| 2 | 6 | 9 | 5 | 33 | $1.9 \times 10^6$ | $4.3 \times 10^7$ | 880 |
| 3 | 6 | 6 | 5 | 29 | $2.3 \times 10^6$ | $4.8 \times 10^7$ | 860 |
| 4 | 7 | 6 | 5 | 27 | $1.9 \times 10^6$ | $3.9 \times 10^7$ | 1600 |
| 5 | 7 | 9 | 5 | 34 | $2.0 \times 10^6$ | $3.8 \times 10^7$ | 1450 |
| 6 | 7 | 6 | 5 | 27 | $2.4 \times 10^6$ | $4.1 \times 10^7$ | 1500 |

TABLE 4-continued

| | | | Twisted Combination Yarns | | | | |
|---|---|---|---|---|---|---|---|
| Sample No. | Example No. | Reaction Time (hours) | Twist Number per Inch | Percent Shrinkage (%) | Initial Young's Modulus (dyne/cm$^2$) | Young's Modulus (dyne/cm$^2$) at Original Length | Tensile Strength (%) |
| 7 | 8 | 9 | 10 | 25 | $2.8 \times 10^6$ | $7.0 \times 10^7$ | 890 |
| 8 | 8 | 9 | 20 | 19 | $3.3 \times 10^6$ | $8.9 \times 10^7$ | 930 |

From the foregoing results, it will readily be understood that the twisted combination yarn of the present invention shrinks on absorption of water and shows rubbery properties while retaining a high strength.

Application Examples of the twisted combination yarn of the present invention will now be described.

APPLICATION EXAMPLE 1

Figure 5:
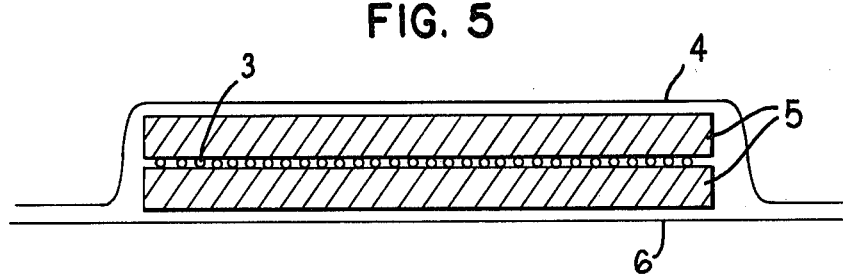
FIG. 5 is a view showing the cross section of an absorbent article including a twisted combination yarn according to the present invention.
Figure 6:
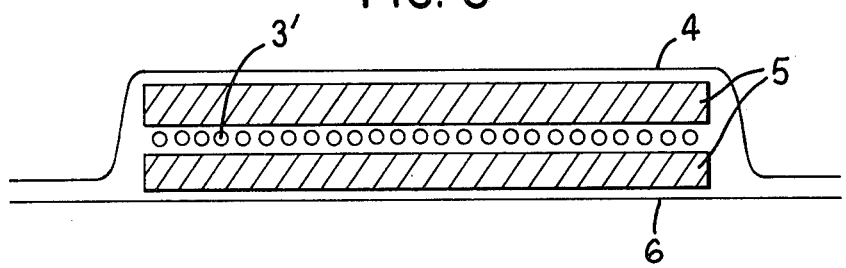
FIG. 6 is a cross-sectional view showing the state where the absorbent article shown in FIG. 5 absorbs water.

As shown in FIG. 5, 26 g of cotton-like pulp (supplied by Weyerhaeuser Co.) was divided into halves to form absorbents 5, and 5 g of the twisted combination yarn obtained in Example 6 by conducting the reaction for 9 hours was aligned between the absorbents 5 as indicated by reference numeral 3. A fusion-bonded non-woven fabric comprising 45% of polyester fibers and 55% of ES fibers and having a basis weight of 20 g/m$^2$ was used as a surface sheet 4, and a polyethylene sheet having a basis weight of 25 g/m$^2$ was used as a back sheet 6 to form a structure shown in FIGS. 5 and 6. In FIG. 6, reference numeral 3' represents the twisted combination yarn which has absorbed water. The properties of the so obtained absorbing article, that is, the absorbing time and return amount, are shown in the following Table.

TABLE

| | Absorbing Time (seconds) | Return Amount (g) |
|---|---|---|
| Absorbent Article Including Twisted Combination Yarn of Present Invention | 76 | 1.7 |
| Absorbing Article Comprising Cotton-Like Pulp (30 g) Alone | 92 | 2.6 |

The absorbing time and return amount were determined according to the following procedures.

A hole having a diameter of 1 cm was formed on a vessel placed on the surface of the absorbing article, and the time required for 60 cc of artificial urine to be absorbed through the hole was measured. This time was defined as the absorbing time. After 2 minutes from completion of absorption of the artificial urine, a load of 40 g/cm$^2$ was applied to an area of 100 cm$^2$ around the absorbing point, and the liquid leaking from the absorbing article was absorbed in a filter paper and the amount of the absorbed liquid was measured. This amount was defined as the return amount.

From the foregoing excellent results, it is seen that if the twisted combination yarn of the present invention is included in an absorbing article, when the absorbing article is wetted, voids are formed around the twisted combination yarn to increase the amount retained of liquid and reduce the return amount of liquid.

APPLICATION EXAMPLE 2

Figure 7:
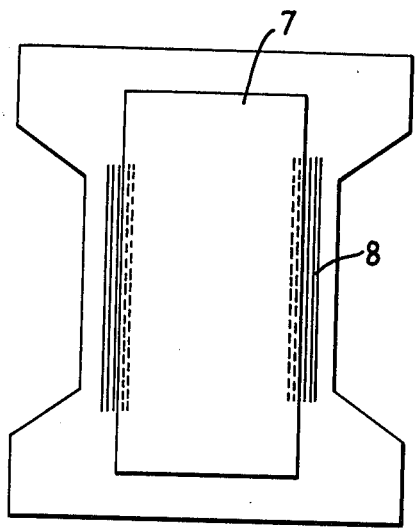
FIG. 7 is a plan view showing a disposable diaper including a twisted combination yarn according to the present invention.
Figure 8:
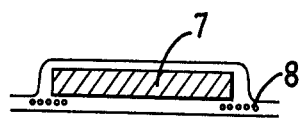
FIG. 8 is a cross-sectional view of the disposable diaper shown in FIG. 7.
Figure 9:
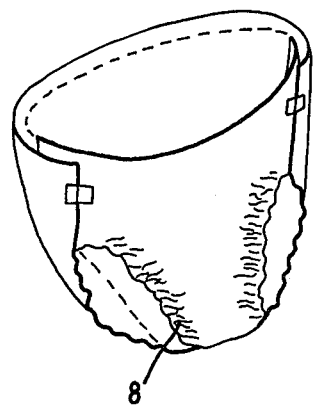
FIG. 9 is a perspective view showing the state where the diaper shown in FIG. 7 is actually used and absorbs water.

As shown in FIGS. 7 and 8, 10 each of the twisted combination yarns (obtained by conducting carboxymethylation for 6 hours) were placed on the left and right crotch portions of a paper diaper at intervals of 1 cm as indicated by reference numeral 8, and the twisted combination yarns were bonded and fixed to the paper diaper by hot melting. Reference numeral 7 represents a water absorbing member. Artificial urine was absorbed on the so obtained diaper. When the artificial urine fell in contact with the twisted combination yarn, the yarn shrunk, and the edge of the diaper adhered closely to the crotch portion as shown in FIG. 9.

The carboxymethylated cellulose yarn improved according to the invention will be illustrated with the following examples.

EXAMPLE 9

Cellulose yarn: Cotton, D.S.: 0.16
Twist type: twisted, three No. 20 count yarns (hereinafter referred to as 20s/3)
Twist coefficient: 3.0

EXAMPLE 10

Cellulose yarn: Cotton, D.S.: 0.23
Twist type: 20s/3
Twist coefficient: 5.0

EXAMPLE 11

Cellulose yarn: Cotton, D.S.: 0.32
Twist type: 20s/3
Twist coefficient: 7.5

EXAMPLE 12

Cellulose yarn: Cotton, D.S.: 0.38
Twist type: 20s/3
Twist coefficient: 7.0

EXAMPLE 13

Cellulose yarn: Cotton, D.S.: 0.16
Twist type: 10s
Twist coefficient: 3.0

EXAMPLE 14

Cellulose yarn: Cotton, D.S.: 0.15
Twist type: 20s
Twist coefficient: 3.5

EXAMPLE 15

Cellulose yarn: Cotton, D.S.: 0.35
Crosslinking agent: Glyoxal
(40% glyoxal is added in an amount of 1%, based on 80% ethanol, to 80% ethanol in an amount of 10 parts by weight per part by weight of carboxymethylated cotton yarn. Then, the carboxymethylated cotton yarn is added thereto and the whole is stirred for 5 minutes. After filtration, the reaction is carried out at 105° C. for 30 minutes.)
Twist type: 20s
Twist coefficient: 3.5

EXAMPLE 16

Cellulose yarn: Cotton, D.S.: 0.65
Crosslinking agent: Glyoxal
Twist type: 20s/3
Twist coefficient: 7.5

EXAMPLE 17

Cellulose yarn: Cotton, D.S.: 0.15
Twist type: 20s/3 (one of the three yarns is non-carboxymethylated cotton yarn)
Twist coefficient: 3.5

EXAMPLE 18

Cellulose yarn: Cotton, D.S.: 0.35
Twist type: 20s/3 (one of the three yarns is non-carboxymethylated cotton yarn)
Crosslinking agent: Glyoxal
Twist coefficient: 3.5

EXAMPLE 19

Cellulose yarn: Polynosic rayon, D.S.: 0.15
Twist type: 30s/3
Twist coefficient: 3.0

EXAMPLE 20

Cellulose yarn: Polynosic rayon, D.S.: 0.25
Twist type: 30s/3
Twist coefficient: 7.0

EXAMPLE 21

Cellulose yarn: Polynosic rayon, D.S.: 0.27
Crosslinking agent: Glyoxal Twist type: 30s/3
Twist coefficient: 3.5

EXAMPLE 22

Cellulose yarn: Cotton, D.S.: 0.35
Twist type: 20s/3
Twist coefficient: 7.5
Direction of twist of single yarn: Z-twist
Direction of twist of the twisted yarn: S-twist

COMPARATIVE EXAMPLE 1

The same as in Example 9 except that D.S. is 0.14.

COMPARATIVE EXAMPLE 2

The same as in Example 9 except that the twist coefficient is 2.8.

COMPARATIVE EXAMPLE 3

The same as in Example 11 except that D.S. is 0.41.

COMPARATIVE EXAMPLE 4

The same as in Example 18 except that two of the three yarns are non-carboxymethylated cotton yarn.

COMPARATIVE EXAMPLE 5

Cellulose yarn: Cotton, D.S.: 0.23
Crosslinking agent: Glyoxal
Twist type: 20s/3
Twist coefficient: 4.0

COMPARATIVE EXAMPLE 6

The same as in Example 19 except that D.S. is 0.14.

COMPARATIVE EXAMPLE 7

The same as in Example 19 except that the twist coefficient is 2.8.

COMPARATIVE EXAMPLE 8

The same as in Example 19 except that the twist coefficient is 2.8.

Contracting power and contraction coefficient of the twisted yarns of Examples 9-22 and Comparative Examples 1-8 upon absorption of water were determined by the following methods.

Contraction power: Power of contraction of the yarn upon wetting with artificial urine (unit: g)

Contraction coefficient: Contraction coefficient = [(original length of yarn) − (length of the contracted yarn)]/(original length) × 100

The embodiments of the invention in which an exclusive property or privilege is claimed are defined as follows:

1. A twisted combination yarn comprising two twisted, plied, first and second yarns, said first yarn being capable of being shrunk in the direction of the yarn length at least 10% of the original yarn length and being capable of being rendered elastic on contact with water, said first yarn consisting essentially of fibers selected from the group consisting of carboxymethylated cellulose fibers, methylated cotton fibers, sulfated cotton fibers, cationized cotton fibers and partially saponified acrylic fibers, and said second yarn consists essentially of fibers which do not shrink more than 10% in length on contact with water.

2. A twisted combination yarn as claimed in claim 1, wherein said cellulose and cotton fibers have a degree of substitution in the range of 0.2 to 0.35.

3. A twisted combination yarn as claimed in claim 1, wherein said first yarn consists of carboxymethylated cotton fibers having an etherification degree of approximately 0.35.

4. A twisted combination yarn as claimed in claim 1, wherein said first yarn consists of methylated cotton fibers having an etherification degree of approximately 0.3.

5. A twisted combination yarn as claimed in claim 1, wherein said first yarn consists of sulfated cotton fibers having an etherification degree of approximately 0.2.

6. A twisted combination yarn as claimed in claim 1, wherein said first yarn consists of cationized cotton fibers having a cationization degree of 0.25.

7. A twisted combination yarn as claimed in claim 1, wherein said first yarn consists of partially saponified acrylic fibers.

8. A twisted combination yarn as claimed in claim 1, wherein said first yarn consists essentially of carboxymethylated cellulose fibers.

9. A twisted combination yarn as claimed in claim 8, wherein said first yarn has a carboxymethylation degree in the range of from 0.15 to 0.40, and a twist coefficient of at least 3.0.

10. A twisted combination yarn as claimed in claim 1, wherein said first yarn consists essentially of crosslinked, carboxymethylated cellulose fibers having a carboxymethylation degree in the range of from 0.25 to 0.7, and a twist coefficient of at least 3.0.

11. A twisted combination yarn as claimed in claim 1, wherein said first yarn is used in an amount of at least 50 weight %, based on the total weight of said twisted combination yarn.

12. A twisted combination yarn as claimed in claim 11, wherein said first yarn is crosslinked with a crosslinking agent selected from the group consisting of glyoxal, epichlorohydrin, ethylene glycol and glycidyl ether.

13. A twisted combination yarn as claimed in claim 9, wherein said first yarn has a contraction power of at least 10 g.

14. A twisted combination yarn as claimed in claim 1, wherein both said first and second yarns are in the form of helices which are intertwined so that when said combination yarn is brought into contact with water, said second yarn forms a radially enlarged, helical sheath within which said first yarn is coaxially disposed, said helical sheath being substantially spaced apart from said first yarn, whereby water can be retained between said first yarn and said sheath.

15. A twisted combination yarn as claimed in claim 9 in which said second yarn consists essentially of cotton fibers.

16. A twisted combination yarn as claimed in claim 10 in which said second yarn consists essentially of cotton fibers.

17. A twisted combination yarn as claimed in claim 9 in which said carboxymethylated cellulose fibers are selected from the group consisting of carboxymethylated cotton fibers and carboxymethylated polynosic rayon fibers.

18. A twisted combination yarn as claimed in claim 10 in which said carboxymethylated cellulose fibers are selected from the group consisting of carboxymethylated cotton fibers and carboxymethylated polynosic rayon fibers.

19. A twisted yarn consisting of from 50 to 100wt. % carboxymethylated cellulose fibers having a carboxymethylation degree of 0.15–0.40 and a twist coefficient K of at least 3.0, wherein $K=T/\sqrt{N}$, T represents the number of twists per inch of said yarn, and N represents the count number of said yarn, and up to 50 wt. % of fibers which do not shrink more than 10% in length when contacted with water.

20. A twisted yarn consisting of from 50 to 100 wt. % of crosslinked carboxymethylated cellulose fibers having a carboxymethylation degree of 0.25–0.7 and a twist coefficient K of at least 3.0, wherein $K=T/\sqrt{N}$, T represents the number of twists per inch of said yarn, and N represents the count number of said yarn, and up to 50 wt. % of fibers which do not shrink more than 10% in length when contacted with water.

21. A twisted combination yarn consisting essentially of two mix-twisted, plied, first and second yarns, said first yarn being a twisted yarn consisting essentially of carboxymethylated cellulose fibers having a carboxymethylation degree of 0.15–0.4 and a twist coefficient K of at least 3.0, wherein $K=T/\sqrt{N}$, T represents the number of twists per inch of said yarn, and N represents the count number of said yarn, said first yarn being used in an amount of at least 50 weight %, based on the total weight of said twisted combination yarn, said second yarn being a twisted yarn consisting essentially of cotton fibers.

22. A twisted combination yarn consisting essentially of two mix-twisted, plied first and second yarns, said first yarn being a twisted yarn consisting essentially of crosslinked carboxymethylated cellulose fibers having a carboxymethylation degree of 0.25–0.7 and a twist coefficient K of at least 3.0, wherein $K=T/\sqrt{N}$, T represents the number of twists per inch of said yarn, and N represents the count number of said yarn, said first yarn being used in an amount of at least 50 weight %, based on the total weight of said twisted combination yarn, said second yarn being a twisted yarn consisting essentially of cotton fibers.

23. A twisted combination yarn as claimed in claim 22, wherein said first fibers are crosslinked by a crosslinking agent selected from the group consisting of glyoxal, epichlorohydrin, ethylene glycol and glycidyl ether.

* * * * *

UNITED STATES PATENT AND TRADEMARK OFFICE
CERTIFICATE OF CORRECTION

PATENT NO. : 4 418 524

DATED : December 6, 1983

INVENTOR(S) : Osamu Ito et al

It is certified that error appears in the above-identified patent and that said Letters Patent is hereby corrected as shown below:

Column 12, Line 67; change "11" to ---10---.

Signed and Sealed this

Fifteenth Day of May 1984

[SEAL]

Attest:

GERALD J. MOSSINGHOFF

Attesting Officer     Commissioner of Patents and Trademarks